(12) United States Patent
Dubreucq et al.

(10) Patent No.: US 8,580,986 B2
(45) Date of Patent: Nov. 12, 2013

(54) PROCESS FOR THE PRODUCTION OF FATTY ACID ALKYL ESTERS

(75) Inventors: Eric Dubreucq, Montpellier (FR); Albrecht Weiss, Langenfeld (DE); Bernhard Gutsche, Hilden (DE); Bernd Fabry, Korschenbroich (DE); Guy Moulin, Montferrier-sur-Lez (FR)

(73) Assignee: Cognis IP Management GmbH, Duesseldorf (DE)

( * ) Notice: Subject to any disclaimer, the term of this patent is extended or adjusted under 35 U.S.C. 154(b) by 619 days.

(21) Appl. No.: 12/304,078

(22) PCT Filed: May 16, 2007

(86) PCT No.: PCT/EP2007/004377
§ 371 (c)(1),
(2), (4) Date: Dec. 9, 2008

(87) PCT Pub. No.: WO2007/140862
PCT Pub. Date: Dec. 13, 2007

(65) Prior Publication Data
US 2010/0234458 A1  Sep. 16, 2010

(30) Foreign Application Priority Data
Jun. 9, 2006 (EP) .................................. 06011909

(51) Int. Cl.
C11C 3/00 (2006.01)
C12P 7/64 (2006.01)

(52) U.S. Cl.
USPC ........... 554/169; 435/134; 435/160; 435/161; 554/163; 554/174

(58) Field of Classification Search
None
See application file for complete search history.

(56) References Cited

U.S. PATENT DOCUMENTS 4,695,411 A    9/1987 Stern et al.
5,316,927 A *  5/1994 Zaks et al. ................. 435/134

(Continued)

FOREIGN PATENT DOCUMENTS

EP   0194165   9/1986
EP   0789079   8/1997

(Continued)

OTHER PUBLICATIONS

Fukuda H,. et al. JP 2000270886 A, 200, English Translation, (11 pages).*

(Continued)

*Primary Examiner* — Yate K Cutliff
(74) *Attorney, Agent, or Firm* — Servilla Whitney LLC

(57) ABSTRACT

Disclosed is an improved process for the production of fatty acid lower alkyl esters according to formula (I)

$$R^1CO\text{—}OR^2 \qquad (I)$$

in which $R^1CO$ represents a linear or branched acyl moiety having from about 6 to about 22 carbon atoms and 0 to 6 double bonds and wherein $R^2$ is a linear or branched alkyl moiety having 1 to 6 carbon atoms, by transesterification of triglycerides or fatty acid esters using $C_1$-$C_6$ aliphatic alcohols, which includes the steps of
(a) providing an aqueous mixture of aliphatic $C_1$-$C_6$ alcohol by fermenting in a first reactor a carbon source comprising carbohydrates and/or glycerol produce a fermentation broth comprising said aliphatic $C_1$-$C_6$ alcohol, (b) providing in a second reactor a triglyceride and/or an ester of a fatty acid, together with a biocatalyst capable of effecting a transesterification reaction, (c) transferring said aqueous aliphatic $C_1$-$C_6$ alcohol mixture obtained from said first reactor into said second reactor to provide a two-phase system, and (d) effecting the transesterification reaction to produce said fatty acid lower alkyl ester and a glycerol- or alcohol-containing aqueous phase.
The products thus obtained are particularly useful as components of the fuel known as biodiesel.

17 Claims, 1 Drawing Sheet

Example:

Flow scheme of the process

(56) References Cited

U.S. PATENT DOCUMENTS

| | | | |
|---|---|---|---|
| 5,710,030 A | | 1/1998 | Anderson |
| 2004/0013708 A1 | * | 1/2004 | Goulson et al. ............... 424/439 |
| 2004/0142441 A1 | | 7/2004 | Weiss et al. |

FOREIGN PATENT DOCUMENTS

| | | | |
|---|---|---|---|
| GB | 1524618 | | 9/1978 |
| GB | 2090514 | | 7/1982 |
| GB | 2090613 | | 7/1982 |
| GB | 2188057 | * | 9/1987 |
| JP | 2000 270886 | | 10/2000 |
| WO | 2005/014765 | | 2/2005 |

OTHER PUBLICATIONS

Nelson, L.A., et al., Lipase-Catalyzed Productin of Biodiesel, 1996, JAOCS, vol. 73, No. 8, pp. 1191-1195.*

Ishige, T., et al., Whole organism biocatalysis, 2005, Current Opinon in Chemical Biology, 9, pp. 174-180.*

Wassenaar T.M., Bacteria: More than Pathogens, 2002, American Institute of Biological Sciences, (4 pages).*

Yeast, http://en.wikipedia.org/wiki/yeast, 2011, (1 page).*

Warwel, S. et al., Substrate selectivity oflipase in esterification of oleic acid, linoleic acid, linolenic acid and their all-trans-isomers and in the transesterification of cis/trans-isomers of linoleic acid methyl ester, 1999, Biotechnology Letters, 21 pp. 431-436.*

Ito, T. et al., Hydrogen and ethanol production from glycerol-containing wastes dischsrged after biodiesel manufacturing process, 2005, Journal of Bioscience and Bioengineering, vol. 100, No. 3, pp. 260-265.*

Jarvis, G.N., et al., Formate and ethanol are the major products of glycerol fermentatin produced by a *Kelbsiella planticola* straqn isolated from red deer, 1997, Journal of Applied Microbiology, 83, pp. 166-174.*

Shaw, J. et al., lipase-catalyzed ethanolysis and isopropanolysis of triglycerides with long-chain fatty acids, 1991, Enzyme Microb. Technol., vol. 13, pp. 544-546.*

Lin, E.C.C., et al., The effect of Aerobic Metabolism on the Inducible Glycerol Dehydrogenase of Aerobacter aerogenes, 1960, The Journal of Biological Chemistry, vol. 235, No. 6, pp. 1824-1829.*

Watanabe, Yomi et al.,Continuous Produciton of Biodiesel fuel form Vegetable Oil Using Immobilized *Candida antarctica* Lipase, 2000, JAOCS, vol. 77, No. 4, pp. 355-360.*

Deng, Li, et al., Enzymatic production of fatty acid alkyl esters with a lipase preparation from *Candida* sp. 99-125, 2003, Eur. J. Lipid Sci. Technol, vol. 105, pp. 727-734.*

*Sacchiromyces cerevisiae*, http:/en.wikipedia.org/siki/Saccharomyces_cervisiae, 2011, 6 pages.*

Edwin S. Olson, et al.: Ester Fuels and Chemicals from Biomass. In: Applied Biochemistry and Biotechnology, vol. 105-108, 2003 pp. 843-851 (XP-009069556).

Clotilde Lecointe, et al.: Ester Synthesis in Aqueous Media in the Presence of Various Lipases. In: Biotechnology Letters, 1996, vol. 18 No. 8 (August) pp. 869-874 (XP-002318361).

Shinobu Oda and Hiromichi Ohta. Coupling of Fermentation and Esterification: Microbial Esterification of Decanoic Acid with Ethanol Produced via Fermentation. In: Biosci. Biotechnol. Biochem., 65 (6), pp. 1388-1390, 2001 (XP-002402991).

S. Alfenore. Aeration Strategy: A Need for Very High Ethanol Performance in *Saccharomyces cerevisiae* Fed-Batch Process. In: Appl. Microbiol Biotechnol (2004) 63: pp. 537-542 DOI 10.1007/soo253-003-1395-5.

European Search Report.

* cited by examiner

Example:
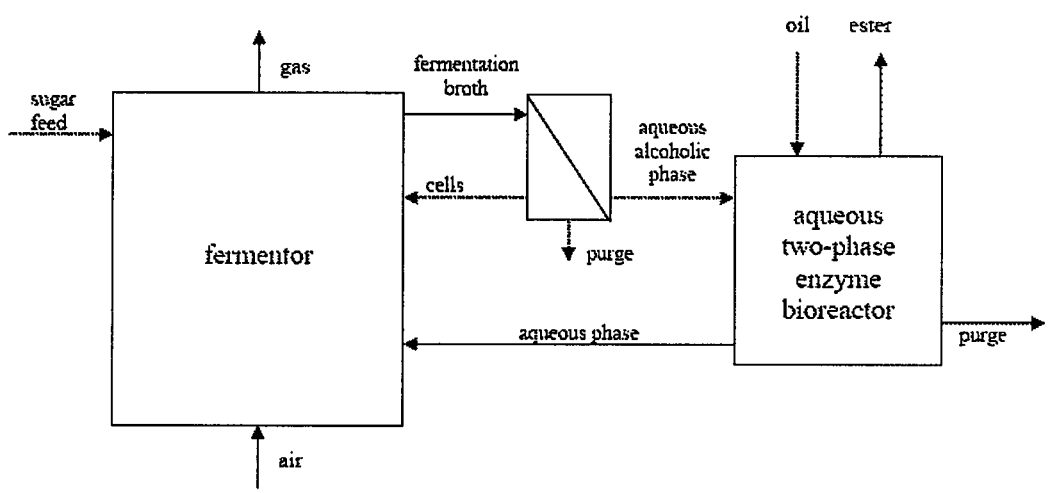
Flow scheme of the process

PROCESS FOR THE PRODUCTION OF FATTY ACID ALKYL ESTERS

CROSS REFERENCE

This application is the National Phase entry of PCT/EP2007/004377, filed May 16, 2007, which claims priority to European patent application number EP 06011909.6, filed Jun. 9, 2006, both of which are incorporated herein by reference in their entireties.

FIELD OF THE INVENTION

The present invention relates to a low-energy process for making biodiesel from carbohydrates and vegetable triglycerides by means of a combination of fermentation and enzymatic transesterification in the presence of water.

BACKGROUND OF THE INVENTION

Nowadays esters from fatty acids and ethanol have obtained a huge economic relevance since these esters—known as "biodiesel"—are used as a substitute for LPG (liquid petroleum gas) or alternatively as an adjuvant for conventional fuels. A major reason for this development is that the esters are based on renewable resources: vegetable oils for the fatty acid part of the molecule and ethanol from the fermentation of starch and other carbohydrates for the ester group. The use of biodiesel therefore represents a contribution to sustainable exploitation of nature rather than the consumption of resources which have been created during billions years and cannot be renewed. This is the major reason for which the European Union has decided to require oil companies to add an increasing amount of biodiesel to LPG based on petrochemicals Commercial processes usually start at present from starch or glucose which are subjected to fermentation to provide an mixture of ethanol and water. For the future other plant biomass sources like cellulose, lignocellulose, hemicelluloses, straw or wood will be useful for the economic production of biofuels like ethanol. A key issue of such process however is to separate the alcohol from the water, since this is a very energy intensive process. For example, a modern motor fuel ethanol plant has a total energy-consumption of 1.1-1.4 MegaJ per liter of ethanol. Even the newest commercial installations are based on a pressure-cascading technique and consume 3.0-4.2 kg of steam for every liter of 96 Vol-% ethanol produced. Earlier distillation systems required 6 kg of steam per liter of ethanol. Unfortunately, the typical transesterification processes do not allow the use of aqueous alcohols in the presence of water hydrolysis becomes a competitive reaction to transesterification. As a matter of fact, according to the state of the art, water is separated out of the transesterification reaction to avoid unwanted side-reactions Thus, it would be highly desirous to develop a process which would avoid any energy-consuming procedure to separate or even reduce the water content in ethanol obtained from fermentation in order to make a transesterification possible, that provides high conversion and selectivity, although conducted under aqueous conditions. The problem underlying the present invention has therefore been to develop such processes in order to reduce costs for the manufacture of biodiesel and to make this important raw material available at lower prices.

BRIEF DESCRIPTION OF THE DRAWING

FIG. 1 is a schematic flow diagram of an embodiment of the process of this invention.

DETAILED DESCRIPTION OF PREFERRED EMBODIMENTS

The present invention claims a process for the production of fatty acid lower alkyl esters according to formula (I)

$$R^1CO\text{—}OR^2 \qquad (I)$$

in which $R^1CO$ represents a linear or branched acyl radical having 6 to 22 carbon atoms and 0 or 1 to 6 double bonds and $R^2$ for a linear or branched alkyl radical having 1 to 6 carbon atoms, by transesterification of triglycerides or fatty acid esters with $C_1$-$C_6$ aliphatic alcohols, which is characterised in that (a) in a first reactor a source of carbohydrates is subjected to fermentation to provide a broth mainly consisting of an aqueous aliphatic $C_1$-$C_6$ alcohol, preferably ethanol, (b) in a second reactor a triglyceride and/or an ester of a fatty acid with an higher alcohol is placed together with a biocatalyst capable to effect a transesterification reaction, and (c) said aqueous aliphatic $C_1$-$C_6$ alcohol, preferably ethanol obtained from the first reactor is transferred into the second reactor in order to effect the transesterification reaction in a two-phase system.

The present invention provides for the first time a process for the production of alkyl esters, particularly useful as so-called biodiesel, which overcomes the disadvantages of the prior art as stated above. In particular, the energy input for production of the alkyl esters is significantly decreased, mainly by using the water-based fermentation broth directly as an alcohol source for the transesterification while at the same time avoiding all the known disadvantages of conducting such process under aqueous conditions. In addition, the process represent a closed cycle, since the by-products like glycerol or glycerol derivatives can also be used, in particular as feed for growing the alcohol-producing biocatalysts. Finally, taking into account that all starting materials are obtained from renewal resources the present invention represents a contribution to sustainable production of industrial products.

Step 1: Fermentation

The production of the lower aliphatic alcohol, preferably ethanol, is conducted by fermentation of a carbohydrate source, like for example starch, inulin, cellulose or lignocellulose in the presence of suitable yeast or bacteria. It is desirous to use yeasts in a food grade quality. The fermentation can be carried out in a temperature range of 20 to 80° C., depending on the conditions according to which the yeast or bacteria shows its optimal productivity. The process can be conducted in any suitable vessel, in a batch, semi-batch or continuous manner. The product obtained typically comprises 5 to 30% by weight (b.w.) aliphatic $C_1$-$C_6$ alcohol and 70 to 95% b.w. water. In addition it should be noted that studies have shown that no specific production rate of ethanol by yeasts increase by more than 400% when ethanol concentration falls from 100 g/L down to 90-95 g/L, so that a self regulation of ethanol production takes place. It may also be possible to have free fatty acids used as carbon substrate by yeast, either during the main operation or in the final biomass production phase. Free fatty acids and also sterols are susceptible to yeast metabolism when dissolved oxygen concentration is low. Another point is that yeasts can incorporate free fatty acids to some extent which increases the nutritional value of the biomass thus obtained.

Step 2: Transesterification

The aqueous aliphatic alcohol is transferred from the fermentation reactor into the second reactor where the two-phase enzymatic transesterification takes place. The nature of the triglycerides used as starting materials is not critical. Basically, all oils from renewable resources can be used depending on what carbon-chain distribution and which degree of unsaturation is desired in the final product. Typical examples are palm oil, palm kernel oil, coconut oil, olive oil, rape seed oil, sunflower oil, safflower oil, soy oil, line seed oil, fish oil, beef or pork tallow and their mixtures. The triglycerides can also comprise amounts of free fatty acids, therefore qualities showing an acid value of 0 to 10 are also suitable. As a second group of substrates for transesterification, also esters of fatty acids and short chain alcohols for example according to formula (II) can be used $$R^1CO\text{---}OR^2 \qquad (II)$$

in which again $R^1CO$ represents a linear or branched acyl moiety having 6 to 22 carbon atoms and 0 to 6 double bonds and $R^2$ is a linear or branched alkyl moiety having 1 to 6 carbon atoms. Typical examples are the esters of capric acid, caprylic acid, caprinic acid, lauric acid, myristic acid, palmitic acid, stearic acid, isostearic acid, oleic acid, elaidinic acid, arachidonic acid, gadoleic acid, behenic acid, erucic acid and their technical mixtures which can be obtained from the triglycerides cited above with the same lower alcohols as obtained from the fermentation process.

The biocatalyst to be used in the second step of the inventive process is preferably an enzyme, showing a high acyl transferase activity particularly in the presence of water and no or very low activity for the hydrolysis of ester bonds, in order to allow conducting the process in the presence of water. Typically, such enzymes can be derived from microorganisms belonging to the species *Candida, Kluyveromyces, Geotrichum, Fusarium, Aeromonas, Debaryomyces, Arxula, Zygoascus, Emericella, Aspergillus, Malassezia, Gibberella, Kurzmanomyces, Ustilago, Nocardia, Cordyceps, Mycobacterium, Rhodococcus, Saccharopolyspora, Burkholderia, Corynebacterium, Saccharopolyspora, Pseudomonas, Streptomyces* and *Pichia*.

More particularly, the enzymes are obtained from:
*Aeromonas aerophila,*
*Arxula adeninivorans,*
*Aspergillus fumigatus,*
*Aspergillus niger,*
*Burkholderia cenocepacia,*
*Candida albicans,*
*Candida antarctica* (*Trychosporon oryzae, Pseudozyma antarctica*),
*Candida cylindracea,*
*Candida glabrata,*
*Candida maltosa,*
*Candida parapsilosis,*
*Candida rugosa,*
*Candida tropicalis,*
*Candida viswanathii,*
*Chromobacterium viscosum,*
*Cordyceps bassania,*
*Corynebacterium diphtheriae,*
*Debaryomyces hansenii,*
*Emericella nidulans,*
*Fusarium oxysporum,*
*Fusarium solani,*
*Fusarium sporotrichioides,*
*Geotrichum candidum,*
*Gibberella zeae,*
*Issatchenkia orientalis* (*Candida krusei*),
*Kluyveromyces marxianus* (*C. kefyr, C. pseudotropicalis*),
*Kurzmanomyces* sp.,
*Malassezia pachydermatis,*
*Mucor javanicus,*
*Mycobacterium tuberculosis,*
*Mycobacterium bovis,*
*Mycobacterium avium,*
*Nocardia farcinica,*
*Penicilium camenberti*
*Pichia guilliermondii* (*Candida guilliermondii*),
*Porcine pancreas,*
*Pseudomonas fluorescens,*
*Rhizomucor miehei,*
*Rhizopus javanicus,*
*Rhizopus oryzae,*
*Rhodococcus* sp.
*Saccharopolyspora spinosa,*
*Saccharopolyspora pogona,*
*Streptomyces coelicolor,*
*Thermomyces lanugenosus,*
*Ustilago maydis* and
*Zygoascus hellenicus* and their mixtures. Due to their excellent transesterification behaviour which allows working with fermentation alcohols comprising up to 30% b.w. of water, enzymes from *Candida parapsilosis* or *Candida albicans* are the preferred biocatalysts. It is also advantageous to immobilise the enzymes on suitable carriers as known from the state of the art. Typically, the enzymes are used in an amount of 0.001 to 5 and preferably 0.01 to 1% b.w. —calculated on the total amount of triglycerides and/or fatty acid esters. In case a biocatalyst is chosen which possesses some hydrolytic activity a second enzyme is added to the transesterification process in order to convert free fatty acids, which may have been formed from hydrolysis into the desired lower alkyl esters.

The addition of the lower alcohol, particularly the ethanol from the fermentation step can be conducted also batch-wise, semi-batch or continuously. In order to avoid unwanted formation of free fatty acid it is advantageous that the concentration of the aqueous lower alcohol from fermentation in the second reactor is adjusted to a level, which is always higher than the critical concentration limit where hydrolysis starts as a side reaction. Typically this concentration is 2 to 20 and preferably 5 to 15 b.w. —calculated on the water phase. Once the desired alcohol concentration is reached it is advantageous to maintain this level over the whole transesterification process.

The transesterification process can be conducted at atmospheric pressure and low temperatures of for example 10 to 80° C., depending on the optimal conditions for the biocatalyst to work. Subsequently, the aqueous layer is separated from the organic phase. Typically, for each 10 g of a fatty acid ethyl ester about 1 g of glycerol is produced. Glycerol or higher alcohols can be re-obtained from the aqueous phase for example either by distillation or membrane separation. In order to complete the cycle, the glycerol obtained from the aqueous phase is used as a feed for growing the yeasts or bacteria used in the fermentation step under aerobic conditions. In an alternative the glycerol can be subjected to a second fermentation step in order to produce for example 1,3 propandiol by means of appropriate micro-organisms like *Chlostridium*.

The alkyl esters of the present invention can find application in quite a number of rather different areas. In a further embodiment of the present invention they are used as a fuel or fuel additive, however, they can also be applied for food and feed products, cosmetic applications or as chemical intermediates. Finally, another object of the present invention is to use the yeast biomass or parts of it obtained from the transesterification process for food and feed applications.

Example

Fermentation was performed as described by Alfenore et al. [Appl. Microbiol. Biotechnol. 63:537-542, 2004] in a 20 L fermentor at 30° C., pH 5 regulated with 14% v/v $NH_3$. Aeration was set to 0.2 vvm and stirring adjusted to keep dissolved oxygen to 20% of saturation. The fermentation was performed with an exponential feeding of biotin based on the growth profile (total biotin concentration added 32 μg 1-1).

The fermentor was supplied with a sterile 700 g/L glucose feed using a peristaltic pump. Fermentation was started with a glucose concentration of 100 g 1-1 and inoculated with 1 g/L of a *Saccharomyces cerevisiae* strain previously grown on the same medium. Whenever residual glucose concentration was lower than 20 g 1-1, glucose feeding was carried out to restore a glucose concentration of 100 g 1-1 or 50 g 1-1 respectively when ethanol concentration was lower or higher than 90 g 1-1.

When ethanol concentration in the fermentor reached 110 g/L (i.e. after ~15 h), the enzyme bioreactor was continuously fed with the fermentation liquid phase, whereas cells were recycled into the fermentor. The aqueous phase from the enzyme bioreactor, containing remaining ethanol (100 g/L) and glycerol from transesterification was also continuously recycled into the fermentor. The enzyme bioreactor had no specific pH or temperature control and worked in the conditions set by the fermentor (pH 5, 30° C.). The bioreactor contained 3500 U (~350 mg) of immobilized lipase/acyltranferase from *C. parapsilosis* per liter of fermentation broth (one U is the amount of enzyme that catalyses the release of 1 μmol ethyl ester/min in the presence 2M ethanol and rapeseed oil at 30° C., pH 5). In these conditions, biomass concentration was 20 g/L (dry weight) and produced 10 g ethanol/L/h when ethanol concentration was 110 g/L. The ethanol produced was converted into 67 g/L/h ethyl ester by enzymatic transesterification of rapeseed oil.

After 15 h of transesterification, the fermentor contained 110 g/L ethanol and 100 g/L glycerol in the supernatant. At this time, total amount of ester produced by transesterification was 1 kg/L fermentation broth. The main production step was then terminated by stopping the glucose feed and the enzyme bioreactor was switched to another fermentor in production.

After glucose depletion by fermentation, the yeast in the original fermentor started oxidizing ethanol, glycerol and free fatty acids (from oil or released in the enzyme bioreactor by residual hydrolytic side-reaction), leading to a final production of 140 g/L fodder yeast biomass after complete oxidation of substrates.

The whole process converted, for 1 L of fermentation medium, 550 g glucose and 950 g rapeseed oil into 1000 g ethyl ester and 140 g yeast biomass. A flow scheme of the process is given in the following FIG. 1.

The invention claimed is:
1. A process for the production of fatty acid lower alkyl esters according to formula (I)

$$R^1CO-OR^2 \qquad (I)$$

wherein $R^1CO$ represents a linear or branched acyl moiety having from about 6 to about 22 carbon atoms and 0 to 6 double bonds, and wherein $R^2$ is a linear or branched alkyl moiety having 1 to 6 carbon atoms, by transesterification of triglycerides or fatty acid esters using $C_1$-$C_6$ aliphatic alcohols, comprising:
(a) providing an aqueous mixture of an aliphatic $C_1$-$C_6$ alcohol by fermenting in a first reactor a carbon source comprising carbohydrates and/or glycerol to produce a fermentation broth of said aliphatic $C_1$-$C_6$ alcohol containing 5 to 30% by weight aliphatic $C_1$-$C_6$ alcohol and 70 to 95% by weight water,
(b) providing in a second reactor a triglyceride and/or an ester of a fatty acid, together with a biocatalyst capable of effecting a transesterification reaction immobilized on a carrier, wherein the biocatalyst is a lipase from *Candida parapsilosis* or *Candida albicans*, and is capable of effecting a transesterification reaction with fermentation alcohols comprising only up to 30% b.w. of water when not immobilized on the carrier,
(c) transferring said fermentation broth obtained from said first reactor into said second reactor to provide a two-phase system, and
(d) effecting the transesterification reaction in said second reactor to produce said fatty acid lower alkyl ester and a glycerol- or alcohol-containing aqueous phase.
2. The process of claim 1, wherein said aliphatic alcohol comprises ethanol.
3. The process of claim 1, wherein said carbohydrates are selected from the group consisting of sugars, starches, inulin, cellulose, lignocellulose and mixtures thereof.
4. The process of claim 1, characterised in that wherein said fermenting takes place in the presence of yeasts, bacteria, or both.
5. The process of claim 1, wherein said triglyceride is selected from the group consisting of palm oil, palm kernel oil, coconut oil, olive oil, rape seed oil, sunflower oil, safflower oil, soy oil, linseed oil, fish oil, beef tallow, pork tallow and mixtures thereof.
6. The process of claim 1, wherein said ester of a fatty acid of step (b) is represented by formula (II), $$R^1CO-OR^2 \qquad (II)$$

wherein $R^1CO$ represents a linear or branched acyl moiety having from about 6 to about 22 carbon atoms and 0 to 6 double bonds, and $R^2$ is linear or branched alkyl moiety having 1 to 6 carbon atoms.
7. The process of claim 1, wherein the concentration of the lower alcohol from fermentation in the second reactor is maintained at a level which is always higher than the critical concentration limit where hydrolysis starts as a side reaction.
8. The process of claim 1, wherein the aqueous phase is separated from the organic phase.
9. The process of claim 1, wherein the glycerol obtained from the aqueous phase is used as said carbon source for growing the yeasts or bacteria used in the fermentation step.
10. The process of claim 9 wherein a glycerol-containing aqueous phase from the second reactor is continuously recycled into the first reactor.
11. A process for the production of fatty acid lower alkyl esters according to formula (I)

$$R^1CO-OR^2 \qquad (I)$$

wherein $R^1CO$ represents a linear or branched acyl moiety having from about 6 to about 22 carbon atoms and 0 to 6 double bonds, and wherein $R^2$ is a linear or branched alkyl moiety having 1 to 6 carbon atoms, by transesterification of triglycerides or fatty acid esters using $C_1$-$C_6$ aliphatic alcohols, comprising:

(a) providing an aqueous mixture of an aliphatic $C_1$-$C_6$ alcohol by a fermentation reaction in a first reactor using a carbon source comprising carbohydrates and/or glycerol to produce a fermentation broth of said aliphatic $C_1$-$C_6$ alcohol containing 5 to 30% by weight aliphatic $C_1$-$C_6$ alcohol and 70 to 95% by weight water, (b) providing in a second reactor a triglyceride and/or an ester of a fatty acid, together with a biocatalyst capable of effecting a transesterification reaction immobilized on a carrier, wherein the biocatalyst is a lipase from *Candida parapsilosis* or *Candida albicans*, and is capable of effecting a transesterification reaction with fermentation alcohols comprising only up to 30% b.w. of water when not immobilized on the carrier, (c) continuously transferring said fermentation broth obtained from said first reactor into said second reactor to provide a two-phase system, (d) effecting the transesterification reaction in said second reactor to produce said fatty acid lower alkyl ester and a glycerol-containing aqueous phase, and (e) continuously recycling the glycerol-containing aqueous phase into the first reactor for use as a feed for the fermentation reaction.

12. The process of claim 11 wherein fermentation is carried out by growth of *Saccharomyces cerevisiae*.

13. The process of claim 11 wherein the fermentation is carried out by growth of yeast and yeast biomass from the fermentation reaction is used for preparing a food or food additive.

14. The process of claim 11 further comprising adding the fatty acid lower alkyl esters to fuel.

15. The process of claim 11 further comprising adding the fatty acid lower alkyl esters to a food.

16. The process of claim 11 further comprising adding the fatty acid lower alkyl esters to a cosmetic formulation.

17. The process of claim 11 further comprising using the fatty acid lower alkyl esters as a chemical intermediate.

* * * * *